(12) United States Patent
Shalon

(10) Patent No.: US 8,882,749 B2
(45) Date of Patent: Nov. 11, 2014

(54) TISSUE-ANCHORED DEVICES

(75) Inventor: Tidhar Shalon, Tel-Aviv (IL)

(73) Assignee: SVIP 8 LLC, Palo Alto, CA (US)

( * ) Notice: Subject to any disclaimer, the term of this patent is extended or adjusted under 35 U.S.C. 154(b) by 111 days.

(21) Appl. No.: 12/995,691

(22) PCT Filed: Jun. 2, 2009

(86) PCT No.: PCT/IL2009/000551
§ 371 (c)(1),
(2), (4) Date: Dec. 2, 2010

(87) PCT Pub. No.: WO2009/147670
PCT Pub. Date: Dec. 10, 2009

(65) Prior Publication Data
US 2011/0166556 A1    Jul. 7, 2011

Related U.S. Application Data

(63) Continuation of application No. PCT/IL2008/000749, filed on Jun. 3, 2008.

(60) Provisional application No. 61/136,378, filed on Sep. 2, 2008.

(51) Int. Cl.
*A61B 17/00* (2006.01)
*A61F 5/00* (2006.01)
*A61M 31/00* (2006.01)
*A61N 1/05* (2006.01)

(52) U.S. Cl.
CPC ............ *A61F 5/0079* (2013.01); *A61M 31/002* (2013.01); *A61N 1/0509* (2013.01); *A61N 1/0517* (2013.01); *A61F 5/0026* (2013.01)

USPC .............................................. 606/1; 606/191

(58) Field of Classification Search
CPC ............................ A61F 5/0003; A61F 5/0079
USPC ............. 606/1, 153, 157; 607/40; 623/23.68; 604/516, 909, 910
See application file for complete search history.

(56) References Cited

U.S. PATENT DOCUMENTS 3,568,678 A * 3/1971 Pourquier et al. ............ 604/174
4,485,805 A * 12/1984 Foster, Jr. ...................... 128/898

(Continued)

FOREIGN PATENT DOCUMENTS

WO  WO 2005/009288    2/2005
WO  WO 2008/003097    1/2008

(Continued)

OTHER PUBLICATIONS

Office Action Dated Mar. 25, 2012 From the Israel Patent Office Re. Application No. 197198 and Its Translation Into English.
Official Action Dated Apr. 18, 2011 From the US Patent and Trademark Office Re. U.S. Appl. No. 12/310,359.

(Continued)

*Primary Examiner* — Lynsey Crandall
*Assistant Examiner* — Nathan J. Jenness
(74) *Attorney, Agent, or Firm* — Ash Tankha; Lipton, Weinberger & Husick

(57) ABSTRACT

A therapeutic or diagnostic device is provided. The device includes a device body which is positionable within a lumen or passageway within a body and a tether which is attachable at a first end to the device body and at a second end to a tissue region not anatomically associated with the lumen or passageway.

6 Claims, 7 Drawing Sheets

(56) References Cited

U.S. PATENT DOCUMENTS

| | | | |
|---|---|---|---|
| 4,878,905 A | | 11/1989 | Blass |
| 5,156,641 A | | 10/1992 | White |
| 5,185,005 A | * | 2/1993 | Ballantyne .................... 604/174 |
| 5,234,454 A | | 8/1993 | Bangs |
| 5,411,022 A | * | 5/1995 | McCue et al. ................ 600/361 |
| 5,462,528 A | * | 10/1995 | Roewer .................... 604/100.01 |
| 6,231,589 B1 | | 5/2001 | Wessman et al. |
| 6,254,570 B1 | | 7/2001 | Rutner et al. |
| 6,264,700 B1 | | 7/2001 | Kilcoyne et al. |
| 6,338,343 B1 | * | 1/2002 | Augustine et al. ....... 128/207.15 |
| 6,746,460 B2 | | 6/2004 | Gannoe et al. |
| 6,754,536 B2 | | 6/2004 | Swoyer et al. |
| 6,971,395 B2 | | 12/2005 | Edwards et al. |
| 7,309,344 B2 | * | 12/2007 | Bakos et al. .................. 606/190 |
| 7,316,716 B2 | | 1/2008 | Egan |
| 7,430,450 B2 | | 9/2008 | Imran |
| 2002/0103424 A1 | | 8/2002 | Swoyer et al. |
| 2003/0208183 A1 | | 11/2003 | Whalen et al. |
| 2004/0030347 A1 | | 2/2004 | Gannoe et al. |
| 2004/0185083 A1 | | 9/2004 | Dionne et al. |
| 2005/0177181 A1 | | 8/2005 | Kagan et al. |
| 2005/0283246 A1 | | 12/2005 | Cauthen, III et al. |
| 2006/0020278 A1 | | 1/2006 | Burnett et al. |
| 2006/0079944 A1 | | 4/2006 | Imran |
| 2006/0282127 A1 | | 12/2006 | Zealear |
| 2007/0021736 A1 | | 1/2007 | Johnson |
| 2007/0080188 A1 | | 4/2007 | Spence et al. |
| 2007/0162085 A1 | | 7/2007 | DiLorenzo |
| 2007/0246052 A1 | | 10/2007 | Hegde et al. |
| 2007/0250020 A1 | | 10/2007 | Kim et al. |
| 2007/0250132 A1 | * | 10/2007 | Burnett .......................... 607/40 |
| 2008/0004598 A1 | | 1/2008 | Gilbert |
| 2008/0091247 A1 | | 4/2008 | Muller et al. |
| 2008/0221599 A1 | | 9/2008 | Starksen |
| 2009/0018606 A1 | * | 1/2009 | Sparks et al. .................. 607/40 |
| 2009/0187230 A1 | | 7/2009 | DiLorenzo |
| 2009/0247992 A1 | | 10/2009 | Shalon et al. |
| 2010/0305656 A1 | | 12/2010 | Imran et al. |
| 2012/0165855 A1 | | 6/2012 | Shalon et al. |

FOREIGN PATENT DOCUMENTS

| | | |
|---|---|---|
| WO | WO 2008/023374 | 2/2008 |
| WO | WO 2008/132745 | 11/2008 |
| WO | WO 2008/149347 | 12/2008 |
| WO | WO 2009/072115 | 6/2009 |
| WO | WO 2009/147670 | 12/2009 |

OTHER PUBLICATIONS

English Summary of Notice of Rejection Dated May 22, 2012 From the Japanese Patent Office Re. Application No. 2009-525171.
Notice of Allowance Dated Aug. 3, 2012 From the US Patent and Trademark Office Re. U.S. Appl. No. 12/451,850.
Supplementary European Search Report and the European Search Opinion Dated Oct. 31, 2011 From the European Patent Office Re. Application No. 09758014.6.
Office Action Dated Jan. 12, 2011 From the Israel Patent Office Re. Application No. 197198 and Its Translation Into English.
Official Action Dated Mar. 14, 2012 From the US Patent and Trademark Office Re. U.S. Appl. No. 12/451,850.
Examiner's Report Dated Mar. 21, 2012 From the Australian Government, IP Australia Re. Application No. 2007287201.
Communication Pursuant to Article 70(2) and 70a(2) EPC Dated Nov. 17, 2011 From the European Patent Office Re. Application No. 0978014.6.
Response Dated Mar. 24, 2011 to Office Action Dated Jan. 12, 2011 From the Israel Patent Office Re. Application No. 197198.
Notice of Allowance Dated Nov. 18, 2011 From the US Patent and Trademark Office Re. U.S. Appl. No. 12/310,359.
International Preliminary Report on Patentability Dated Apr. 9, 2009. 2009 From the International Bureau of WIPO Re.: Application No. PCT/IL2007/001047.
International Preliminary Report on Patentability Dated Dec. 16, 2010 From the International Bureau of WIPO Re. Application No. PCT/IL2009/000551.
International Preliminary Report on Patentability Dated Jan. 28, 2010 From the International Bureau of WIPO Re.: Application No. PCT/IL2008/000749.
International Search Report and the Written Opinion Dated Oct. 13, 2009 From the International Searching Authority Re.: Application No. PCT/IL09/00551.
International Search Report Dated Jul. 3, 2008 From the International Searching Authority Re.: Application No. PCT/IL07/01047.
international Search Report Dated Nov. 13, 2008 From the international Searching Authority Re.: Application No. PCT/IL08/00749.
Written Opinion Dated Jul. 3, 2008 From the International Searching Authority Re.: Application No. PCT/IL07/01047.
Written Opinion Dated Nov. 13, 2008 From the International Searching Authority Re.: Application No. PCT/IL08/00749.
Response Dated Jun. 21, 2011 to Official Action of Apr. 18, 2011 From the US Patent and Trademark Office Re. U.S. Appl. No. 12/310,359.
Restriction Official Action Dated Feb. 8, 2012 From the US Patent and Trademark Office Re. U.S. Appl. No. 12/451,850.

* cited by examiner

US 8,882,749 B2

TISSUE-ANCHORED DEVICES

RELATED APPLICATIONS

This Application is a National Phase of PCT Patent Application No. PCT/IL2009/000551 having International filing date of Jun. 2, 2009, which claims the benefit of U.S. Provisional Patent Application No. 61/136,378 filed on Sep. 2, 2008, and which is also a continuation of PCT Patent Application No. PCT/IL2008/000749 having International filing date of Jun. 3, 2008. The contents of the above Applications are all incorporated herein by reference.

FIELD AND BACKGROUND OF THE INVENTION

The present invention relates to a device, system and method suitable for positioning and optionally anchoring devices with a lumen or passageway of a body.

Various treatment approaches require positioning of devices in body lumens or passageways. For example, devices positioned within the lumen of the gastrointestinal (GI) tract are utilized in a variety of gastrointestinal procedures, such as stomach volume reduction, placement of stomach-anchored devices such as electrodes and sphincter repair [e.g. gastro esophageal reflux disorder (GERD) treatment]. Such devices are typically anchored to tissues surrounding/forming the passageway or lumen to ensure accurate positioning of the device.

Current devices are limited by the strength of anchoring and are further hampered by complicated and clinically invasive anchoring procedures. Most currently utilized anchors utilize a soft or hard tissue anchoring element for penetrating and anchoring to a tissue encompassing the passageway or lumen and a short length of suture which is attached to a device body. Although such anchor configurations are designed to have some compliance under pull forces by virtue of the suturing path, the inelastic nature of the suture portion of the anchor oftentimes leads to tissue tearing, erosion, infections, device migration, and anchor dislodgement. In the GI tract with intense peristalsis, in-tissue anchor elements are exposed to significant mechanical forces and a harsh chemical environment, making long term anchoring very difficult with presently available anchor designs.

Although a variety of anchor designs attempt to solve these problems, very few approaches manage to achieve adequate long lasting fixation of devices to soft tissue of the GI tract. In addition, positioning a device body within a lumen (e.g. stomach lumen) and anchoring it via a tether to tissue surrounding the lumen (e.g. stomach wall) requires complicated open, laparoscopic or endoscopic procedures.

While reducing the present invention to practice the present inventors have devised a novel anchoring scheme which traverses the limitations of presently described anchoring approaches and provides long lasting and easily deployable anchoring of devices in a lumen or passageway of the body.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
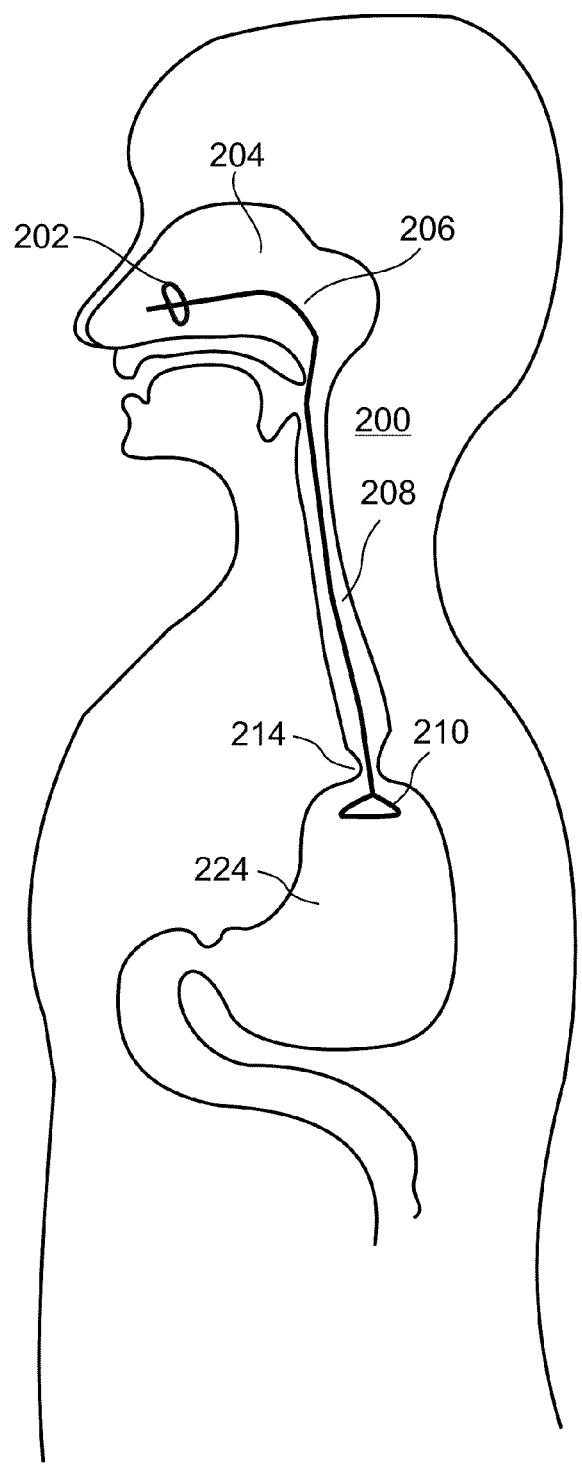
FIGS. 1A-B depict in sagittal view an anti-reflux barrier positioned in the lower esophageal sphincter tethered through the esophagus and anchored in the nasal septum.

The present invention is of a novel anchoring approach which can be used to facilitate positioning of devices within a lumen or passageway of a body.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As is mentioned hereinabove, prior art intraluminal devices which are anchored to tissues surrounding the lumen are prone to tissue erosion, anchor failure and in addition are complicated by complicated invasive anchoring procedures.

The present inventors have devised an anchoring approach which greatly simplifies anchoring and device positioning while at the same time enabling easy device delivery and retrieval, as well as device positioning adjustments.

The following describes several exemplary applications of the novel device positioning and anchoring approach of the present invention. As used herein, the term lumen refers to any interior space within a body tissue, while the term passageway refers to a fluid or gas conduit. The phrase "tissue region not anatomically associated with a lumen or passageway" refers to a tissue region within the body which has at least one anatomical function distinct from the lumen or passageway.

GERD

Gastroesophageal reflux disorder (GERD) is a condition in which the esophagus becomes irritated or inflamed because of acid or other fluids such as bile or water backing up from the stomach into the esophagus (reflux).

Approaches for treating GERD include lifestyle changes, medication and endoscopic procedures. Proton pump inhibitors (PPIs) represent the mainstay of therapy for patients with non-erosive reflux disease (NERD), and while modern technologic advances in endoscopic procedures have improved the efficacy of endoluminal GERD therapy, currently practiced approaches are still limited in as far as long term efficacy. Many of the endoscopic suturing devices (such as Bard's Endocinch™) try to use inelastic sutures to modify the natural anatomy of the lower esophageal sphincter (LES). The sutures end up eroding through the tissue which is constantly working against the sutures, and therefore the procedure loses its effectiveness over time.

Although numerous devices for treating GERD have been described in the patent literature (see, for example, U.S. Pat. Nos. 4,846,836; 5,314,473; 5,861,036 and 6,264,700), such devices are designed to replace rather than augment the function of the LES and as such are bulky and intrusive and thus may lead to migration, erosion, dysphagia as well as other morbidities. Furthermore, many endoscopic funduplication techniques exist (for example NDO™ surgical, Esophyx™ from EndoGastric Solutions Inc, and Medigus™), but these are quite complicated procedures and expensive devices requiring significant training, lengthy anesthesia and operating room times, and the expertise of a surgeon in addition to the endoscopist for implementation. Furthermore these techniques are generally not reversible, thus making them less attractive for patients.

The present inventors propose that effective GERD treatment can be accomplished without altering the anatomy of the LES or surrounding regions of tissue while doing so in a fully reversible and non-invasive manner.

A device for treating GERD can be constructed by suspending a device body from nasopharyngeal or orpharyngeal tissues via a tether, and configuring the tether length and device body design so as to block reflux in the LES region of the esophageal lumen. Such tethering can be facilitated via a soft or hard, elastic or a non-elastic tether (made from polymers such as a variety of plastics, silicone, polyurethane or the like with a diameter of 0.1-5 mm) which is anchored at its proximal end to nasopharyngeal tissue (e.g. nostril or nasal septum) and is attached at its distal end to the device body.

Tethering is effected such that the device body is preferably suspended above, in or under the LES in a position which lies in the path of reflux, preferably at a position such that a reflux episode pushes the device body against the lower or lateral LES surfaces, thereby blocking the esophageal lumen and preventing reflux from passing into the esophagus.

Figure 1B:
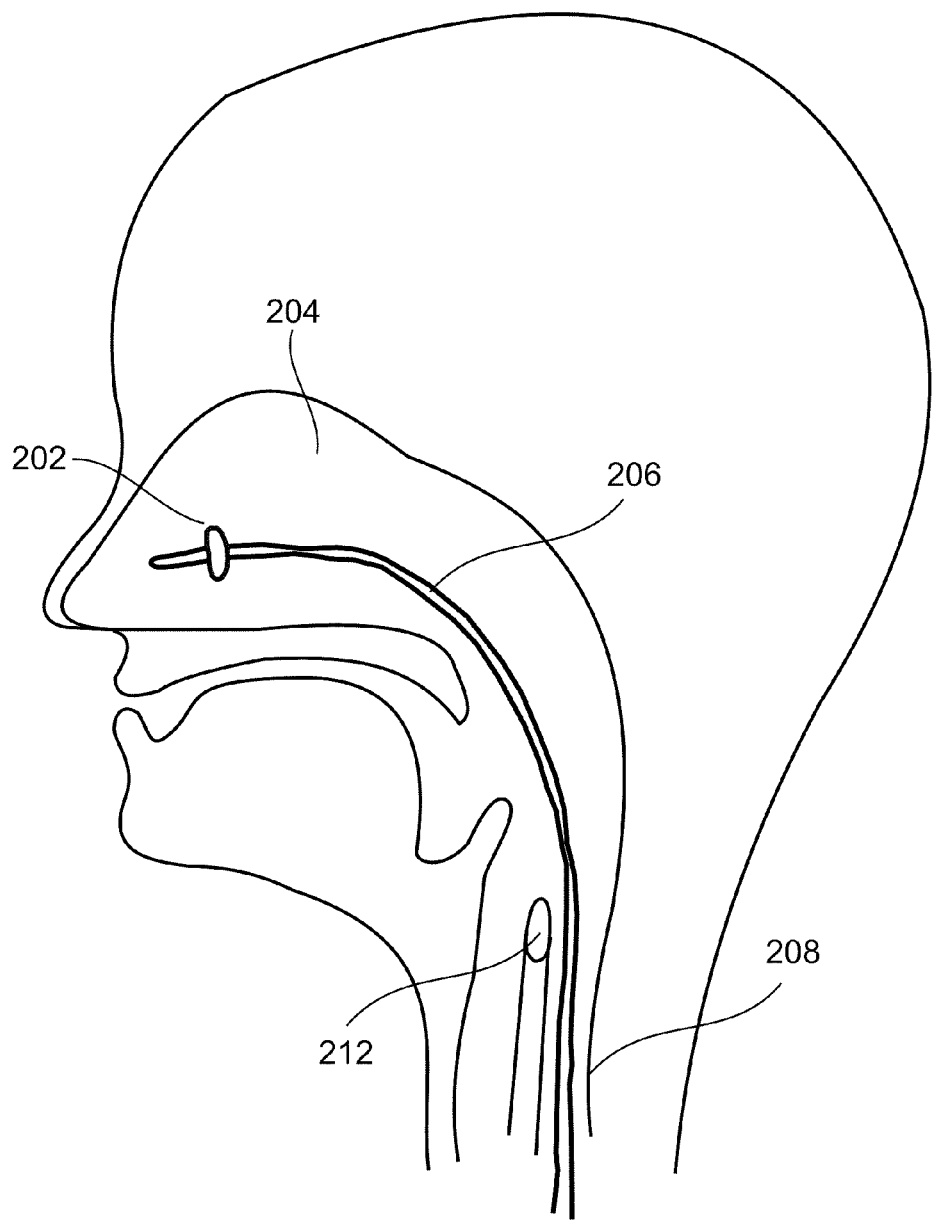

One embodiment of a GERD device constructed in accordance with the teachings of the present invention is shown in FIGS. 1a-b. Such a device, which is designated as device 200 includes a device body 210 which is attached to a solid tether 206 which is anchored using anchor 202 to the nasal septum in nasopharynx 204. Solid tether 206 runs down esophagus 208 and is attached to anti-reflux device body 210 sitting just below lower esophageal sphincter 214 at the top part of stomach 224. FIG. 1b illustrates the area of nasopharynx 204 in greater detail, including cricoid cartilage 212.

Device body 210 can be circular, conical or cylindrical in shape with or without a rim or disc at its distal tip. Such a device body 210, which can be anywhere from 1 to 30 mm in diameter and 0.01 to 3 mm thick, preferably 10-20 mm in diameter and 0.1-0.3 mm thick and form a conical guard or shield around which the LES contracts to improve the seal against reflux, yet does not significantly interfere with the diameter of the lumen when the LES is open for the passage of a food bolus due to the small size or collapsibility of device body 210. Such device body 210 can be of a prefixed size made from elastic material such as silicone or hollow (or fluid filled) to allow the proper volume for internal bulking to alleviate GERD.

The seal between device body 210 and the LES can be selective and thus allow natural passage of gas, during for example, burping and yet block passage of liquids. In the example section hereinbelow, a human volunteer fitted with device 200 reported the ability to burp while the anti-reflux device was in place, indicating that gas can escape around such a device when properly sized and configured. During peristaltic waves, e.g. swallowing saliva, drinking water or eating food, the device can collapse, be pushed to the side of the esophageal lumen, or pushed into the stomach by the stretching of the elastic tether, and then resume its position of sealing the esophagus at the end of the peristaltic wave.

Additional configurations of GERD device bodies and systems are described in PCT application number PCT/IL 2008/000749, also by the present inventors.

Intragastric Devices

Intragastric balloons such as the Bioenterics Intragastric Balloon (BIB™) is a temporary non-operative method helping patients to lose weight by partially filling the stomach, inducing the feeling of satiety and assisting in getting used to proper dietary habits. The balloon is placed in to the stomach via an endoscope and filled with 500-700 cc of blue-colored saline solution, causing it to expand into a spherical shape. The placement of BIB is limited to maximum 6 months, and then it has to be emptied and removed by endoscopy. Two of the major limitations of the intragastric balloon are their initial intolerability and migration, both when inflated and if they become deflated.

Thus according to another aspect of the present invention, there is provided an intragastric device which includes a gastric balloon which is attached to a hollow tether that rises up through the esophagus ending in an anchor in or on a nasopharyngeal tissue. The tether can be hollow to enable fluid or gas to be transferred to and from the balloon using a septum in the nasopharynx. This has the advantage of allowing the balloon to be filled gradually over days or weeks without additional endoscopic procedures. Gradual filling gives the patient time to get used to the balloon and will reduce patient discomfort and the number of balloons that are removed right after implantation due to patient intolerance. Furthermore, the tether can also serve to keep the balloon in the stomach and prevent migration and subsequent GI tract obstruction in the event of a leak or balloon deflation. The tether can also serve to enable removal of a deflated balloon through the nose or mouth without further endoscopic intervention.

The device body can have a plurality of separate smaller balloons, with 1-100 cc of fluid each individually tethered to enable independent inflation or deflation of balloon bodies. The device body or bodies can also be compressed and deploy once exposed to the low pH of the stomach environment.

Device body 210 or 228 can be floating in the stomach or pulled against the proximal surface of the stomach to recreate the effect of anti-obesity Lapband™ which also induces pressure on the proximal stomach wall.

Device Residing in the Intestines

Gastric sleeves (as described for example in U.S. Pat. No. 7,476,256) and other devices that reside primarily in the small intestine can be anchored to a non-GI tissue such as the nasopharynx or other tissues as described herein, particularly since the tether can have a minimum profile until it enters the duodenum. A tether with a small transverse cross sectional area (about 0.1-5 sq mm) in the esophagus and stomach ensures that the intense peristaltic waves in these regions have very little to grab on to and don't exert significant tension on the tether. Inside the small intestine, the peristaltic forces are much weaker relative to the stomach, and therefore almost any device, whether it is a bypass sleeve to induce malabsorption, a stimulator, or a flow reduction element, can live in the small intestine with little tension on the upstream tether. Additional example configurations of intestine-resident device bodies and systems that are attachable using the tether schemes of the current invention are described in U.S. patent application U.S. 2005/0192614.

Tissue Stimulation Devices

Tissue stimulation devices are mechanical or electrical devices that activate tissue receptors (e.g. stomach wall receptors) via electrical or tactile stimulation. In gastric applications, such devices can be directly anchored or tethered to the submucosa, muscles or nerves in, outside or around the stomach via endoscopic [e.g. natural orifice transesophageal surgery (NOTES)] or laparoscopic procedures. The purpose of such devices is to alter gastric motility (reduce motility in the case of obesity, increase motility in the case of gastroparesis). For obesity treatments, a reduction of motility induces satiety or increases the duration of satiety thereby making the subject consume less food. A limitation of current gastric stimulators is the need to include a power source, charging or communication circuitry in the device body, therefore making it bulky and allowing for a finite lifetime. Bulky stimulators are not well tolerated in the stomach, as they are churned by stomach tissue and cause tissue erosion or ulceration or become detached and migrate.

Thus according to another aspect of the present invention there is provided a gastric stimulation device which includes a stimulatory device body, e.g electrodes which are implanted in or outside the stomach. The stimulatory device body is connected (directly or through a control unit) via an electrically conductive tether in the esophagus, to an electrical interface anchored in or outside the nasal cavity.

In an electrode embodiment, power and control signals can be provided periodically to the implanted electrodes through a connection to the electrical interface. Furthermore, the electronics and/or power storage elements can be included in the nasopharynx where they are subjected to a much more benign mechanical and chemical environment than the stomach. The present inventors have successfully implanted loops of non-absorbable sutures through stomach tissue of a pig using endoscopic means and observed that no erosion or other long term tissue damage occurred. Using a vacuum cup pushed on the front of an endoscope, an electrode can be implanted at a known depth of stomach tissue and connected via electrically conductive tethers to a control unit, power source and/or electrical interface in the oral or nasal cavity.

Similar approaches can be used to implant mechanical stimulation devices (e.g. vibratory devices) with tethers supplying power and control signals.

Other areas that can be stimulated using the device of the current invention include tissues such as muscles or nerves in or around the nasal cavity or phayrynx. Examples include tissues such as the tongue (for relief of obstructive sleep apnea), the sinuses (for enhanced drainage), the trigeminal nerve (for pain control) or the spheno-palatine ganglion (for permeation of the blood brain barrier). The power and control circuitry for such an embodiment can be resident in the external element 302 (shown in FIGS. 5a-b), and the electrical signals carried through tether 206.

Anti-Obesity Device

Partially or sporadically obstructing the outlet of the stomach is known to create a sense of fullness and early satiety that can lead to weight loss for obese patients.

Thus according to another aspect of the present invention there is provided an anti-obesity device which includes at least one device body which is attached along the length, or at the end of a tether. The device body can be designed to partially occlude the pylorus. In that respect, the device body can be designed as a flat or conical sheet or as a volume occupying object around 0.5-3 cm in diameter which cannot easily extend far beyond the pylorus. The tether length can be adjusted such that smaller elements mounted downstream (distal) on the tether can serve as "sinkers" and be transported deeper into the small intestine or even the large intestine via normal peristalsis to keep the tether running though the pylorus. Also, in the event of a vomiting episode, a device body that resides on a tether that extends deep into the intestines would not be as easily ejected from the stomach. In the event that the device is ejected from the stomach in a vomiting episode, it can simply be re-swallowed with a glass of water and be self-delivered to the intended location based on natural peristalsis and the length of the tether. The pylorus-blocking device body can also be attached in a manner which allows it to slide along the length of the tether so that it can reach the region of the pylorus without the need to pre-measure the length of the tether.

In one specific embodiment, the elastic tether is a 1 mm diameter silicone thread anchored to the nasal septum that extends at least 10 cm beyond the pylorus. The device body is composed of several flat disks or open cones around 10 to 30 mm in diameter which are mounted spaced 1 to 10 cm apart along the length of the tether. The disks therefore partially block the pylorus or pyloric channel or sections of the small intestines, slow down gastric emptying and therefore induce satiety.

Alternatively, the device body can include disks or cones which are larger in diameter or inflatable through the tether such that they more fully block the pylorus or reduce flow of chyme through the pylorus and small intestines by reducing the available cross sectional area of the lumen at various points along the GI tract.

Additional configurations of gastric-resident device bodies and systems that are attachable using the approach of the present invention are described by the present inventors in PCT application number PCT/IL 2007/001047.

Drug Delivery

In addition to facilitating positioning and anchoring of devices, the present invention also enables delivery of fluids to a device anchored within a lumen or passageway or sampling of fluids present in the environment of the device.

Thus, according to another aspect of the present invention there is provided a drug delivery device which is referred to herein as device 220.

Figure 2A:
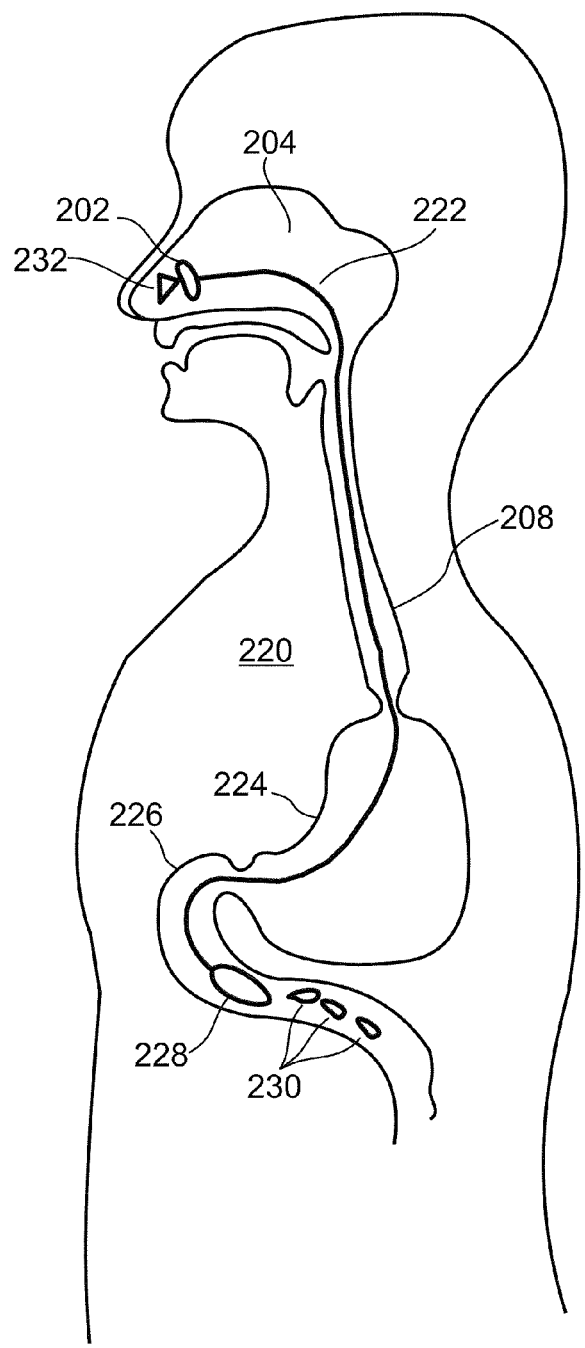
FIGS. 2A-B depict a refillable drug delivery depot anchored in the small intestines and filled through a hollow tube running through the esophagus to a septum in the nasopharynx.
Figure 2B:
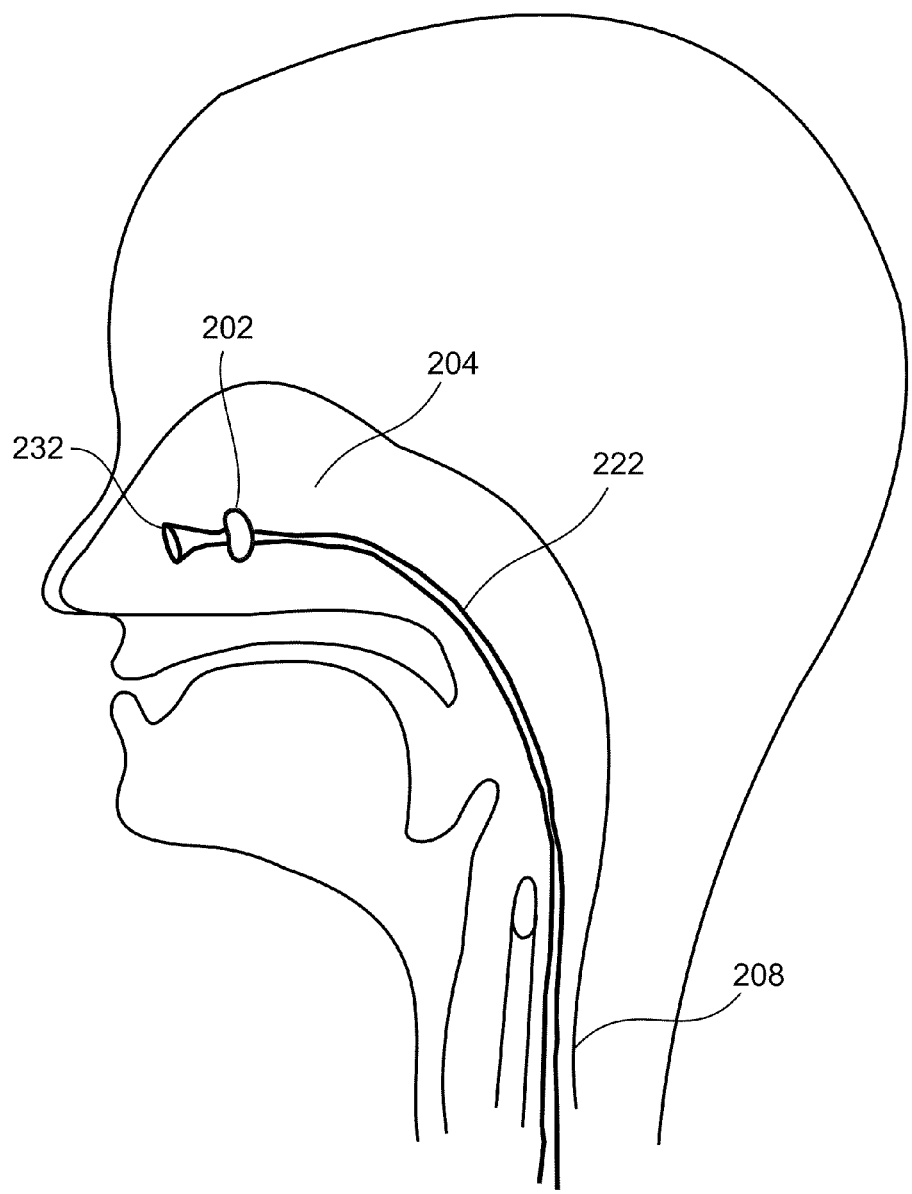

FIG. 2a depicts device 220 which is anchored using anchor 202 to the nasal septum in nasopharynx 204. Interface 232 (for example a puncturable septum) enables injection of active agent 230 into hollow tether 222 which runs down esophagus 208, through stomach 224 and into small intestines 226 and is attached to depot 228 which releases active agent 230 into small intestines 226. FIG. 1b shows the area of nasopharynx 204 in greater detail.

As an example of such an embodiment, the proximal end of hollow tether 222, for example 1 mm OD and 0.6 mm ID silicone tubing, can be anchored in the nasal cavity and the distal end can terminate at the desired location in the GI tract, say in the duodenum. Any active agent 230 injected through interface 232 into the proximal end of hollow tether 222, for example a peptide drug such as insulin or various hormones, would bypass the stomach and be delivered directly to the small intestine. Such a delivery would have the advantage of avoiding drug degradation in the stomach, having fast onset of action, and avoiding the need for a needle stick. The proximal end of hollow tether 222 can have an anchor with a fluidic interface 232 such as a septum or other fitting to enable a short blunt end needle on the end of a standard syringe to interface with hollow tether 222 to facilitate self-administration of the drug by the user in a painless and fast manner. The tether/syringe communication can be facilitated with magnetic clasp so it can be done without direct visualization.

Device 220 can be a passive delivery device for immediate administration of drugs. Alternatively, or additionally, a drug reservoir or depot can be incorporated into device 220 which is in fluid communication with the hollow tether. The drug reservoir or depot can be in or deliver drugs to the sinuses, nasopharynx, oropharynx, pulmonary or GI system. The drug reservoir can be a slow release formulation in a solid or gel-like matrix that elutes the drug or dissolves over time. The drug reservoir or depot can be filled with an active agent in the liquid state and re-filled occasionally by the patient or a healthcare professional and then actively or passively programmed to release drug at the appropriate time, using patient, healthcare professional or closed-loop sensor feedback control. By way of example, the septum of the anchored tether in the nasopharynx can include a one way septum and the drug that is injected into the tether flows into and inflates an elastic device body with an orifice that then releases the drug at a know rate to a region of the small intestine. By way of an additional example, the hollow space in hollow tether 222 can be the reservoir itself.

Example applications of the above system include insulin administration for diabetics, hormone treatments, administration of anti-obesity drugs, localized chemotherapy for lesions in the GI tract, PPIs for neutralizing GERD, localized delivery of therapy for inflammatory bowel conditions such as IBD or Crohn's disease, ulcerative colitis in the colon, and the like. The drug can be injected into the fluid interface in the nasopharynx many times a day (such as for insulin) or once every several months (as in PPIs). The drug delivery reservoir or depot can also be separately and locally anchored to the stomach wall or other region of the GI tract with an anchor such as a T-bar, clip or suture, so that the tether functions only as a filling or inflation port and not as a mechanical anchor. The advantage of this embodiment is to better localize the drug delivery depot and minimize the mechanical forces on the tether, and therefore allow the use of a very small diameter (1 mm or smaller OD), thin wall (0.2 mm or smaller), soft (shore 70 or less) material and hence more comfortable tether.

Diagnostics

The hollow tether of the present invention can be used to sample fluids, measure physiological parameters (e.g. pH, temperature, impedance, pressure, images with different modalities, sugar levels, etc), or view the lumen long term using optical means with tether 206 being made of fiber optics for example. Using the same device, one can then sample such fluids or read such parameters using the fluid, optical or electrical interface on the proximal end of the tether. Appropriate drugs or therapeutic intervention can then be affected using the tether as the conduit to deliver such fluid, electrical or optical therapy to the desired tissue. Tether 206 or 222 can be used as an antenna for exporting or importing information or electrical power. Tether 206 or 222 can have within it multiple lumens or channels, either in parallel or coaxially for various modalities within a single tether.

Other Applications and Features

Tether 206 or 222 described with respect to FIGS. 1a-b and 2a-b can be used to anchor one or more device bodies each addressing a single disorder, for a resulting combination product with two or more indicated uses simultaneously.

Tether 222 can be used as a more comfortable feeding tube for patients what cannot eat normally. Tether 222 can be delivered within or in parallel to a more rigid overtube or pushrod (see example section below). Flexible tether 222 will be considerably more tolerable than the current semi-rigid tubes that are rigid enough to allow them to be pushed into the stomach directly. The feeding tube could be swallowed once past epiglottis, self targeted into duodenum or stomach based on size. The head of the feeding tube can be inflatable or self expanding to allow introduction in a compressed state through nostril. Upon removal, all parts of the device could be collapsible or flexible enough to go back through nostril for removal. Device body 210 or 228 is folded back on introduction and folded forward during withdrawal. A water jet from inside can be directed backwards from distal tip to act as jet advancing tether and device body 210 or 228 through the GI tract. Sequentially inflatable radially-expanding elements at the head of device body 210 or 228 can cause device 200 to advance in a lumen using inch-worm-like propagation.

Device 200 or portions thereof can be coated with water-soluble material, such as a film, to compress or alter the geometry during insertion of device 200 into the body, whereupon after a predetermined time the water soluble material dissolves and device 200 or portions thereof revert to their geometry before water-soluble material was added. For example, tether 206 or 222 can be coated with a water soluble film to make tether 206 or 222 more rigid for introduction into the body without an applicator, once the water-soluble material dissolves in the body, tether 206 or 222 would soften in the body for maximal comfort and not support a pushing force. As a further example, device body 210 or 228 can be compressed into a water soluble sheath for easy introduction into the body and once in the proper position in the lumen, the water soluble material dissolves and device body 210 or 228 resumes its original expanded shape.

Optionally, the tether and attached device body can have graduation markings and be radio-opaque to enable real time or near real time tracking of the device body's position.

The tether and device body can have a variety of cross sectional areas and material hardnesses. For example, the tether can be relatively softer in the part that touches the back of the oropharynx or entrance to the esophagus, as these are very sensitive parts of the anatomy.

The tether and anchor can hook around the cricoids cartilage region (with the open part of the hook in the trachea and the hook going through the interarytenoid notch), or with a stud through the cricoid cartilage into the trachea. Alternatively, the device can anchored with stitch through the soft tissue around the cricoids cartilage. In yet a further embodiment, the device is anchored using a stent in the trachea and the tether is pulled up over interarytenoid notch into esophagus. It is also possible to anchor on other tissues such as into verterbra on posterior wall of esophagus, or the hard or soft palate.

It will be appreciated that any of the configurations described herein can employ a tether having an adjustable length. Such an adjustment can be effected in real time or following the implantation procedure. For example, a hollow tether 222 configuration can be adjusted to the right length at the nostril and excess tether cut off. A metal wire can be introduced into the hollow tether end and then bent to fit around the subject's nasal septum at the entrance to the nostrils, thereby forming a nose clip for the temporary or permanent anchoring of the device. Alternatively, a "nose stud" can be driven across a tissue described above and the tether attached to one or both ends of the stud. A T-anchor element approximately 0.4 to 2 mm (preferably 0.7-1.0 mm) in diameter and 1-10 mm (preferably 4-6 mm) long can be introduced through the nasal septum either deep in the nasal cavity or through the cartilage closer to the nostrils using an slotted hypodermic needle with an internal pushrod for the purpose of anchoring device 200. Such an anchoring scheme is invisible from the outside, takes up almost no volume the nasal cavity and is fully reversible.

Figure 5A:
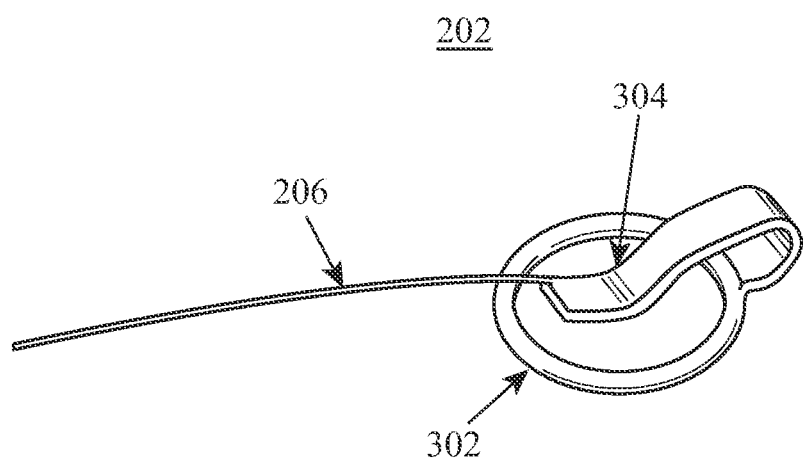
FIGS. 5A-B depict a nose clip anchor used to anchor the tether to the nose of a human subject.
Figure 5B:
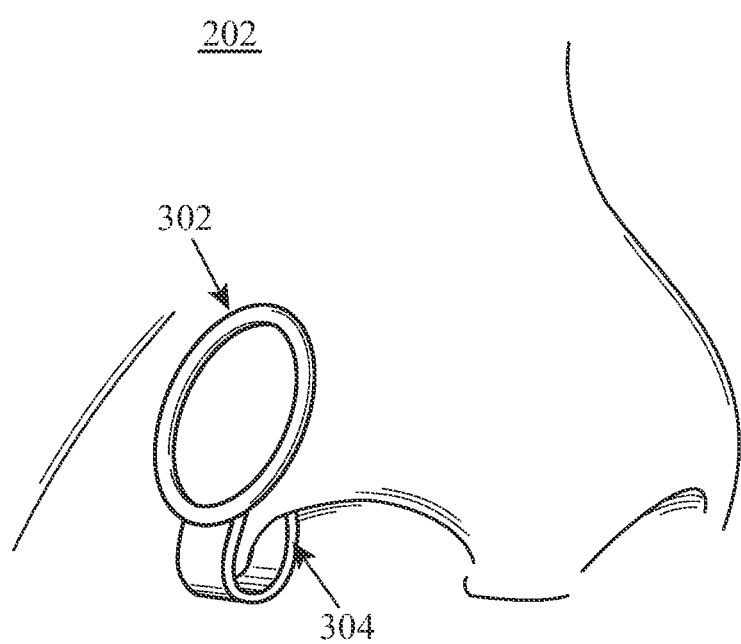

A further embodiment of an anchoring nose clip is illustrated in FIGS. 5a and b. FIG. 5a shows nose clip anchor 202 with an external element 302 that rests on the external surface of a nostril and an internal element 304 to which tether 206 is attached (or equivalently 222). FIG. 5b shows nose clip anchor 202 mounted on the nose of a subject with external element 302 visible. External element 302 is sized to be large enough (e.g. approximately 10-20 mm diameter) so as to not enable passage of anchor 202 into the nasal cavity through the nostril in case anchor 2002 becomes dislodged in any way from its position. It was determined experimentally by the current inventors that bridging the external nostril tissue was more tolerable than bridging the tissue between both nostrils and that it is important to keep the area and volume of internal element 304 of nose clip anchor 202 that resides inside the nostril to an absolute minimum to increase comfort for long term use.

In certain embodiments of the current invention, external element 302 can include a power source (such as a battery or capacitor) and wireless power or data transmission means to communicate with external devices. Tether 206 can connect anchor 202 to sensors or actuators that are driven by the power contained in external element 302 and the power or data collected by such sensors or the power or commands to drive such actuators can be transmitted along tether 206.

The anchor and/or proximal portion of the tether can be cantilevered from the posterior end of the nasal septum to enable tether 206 or 222 to drop down straight into the esophagus, instead of curving along the soft palate and entering the esophagus at a slight angle which may cause it to be felt more strongly than a straight shot down the esophagus. For this purpose, tether 206 or 222 or a portion thereof can be rigid enough to be cantilevered over the top of the soft palate as it curves down towards the oropharynx.

All features and surfaces of any of the devices of the present invention can be coated with materials that provide therapeutic effect or anti-bacterial activity such as Surfacine™ (www.surfacine.com). Such coatings, or alternatively the device materials themselves, can be made of biodegradable materials that disappear over time into the GI system. All, or a portion of the device, can be degradable to allow it to detach after a known time interval and be passed harmlessly through the GI system.

In cases where use of a positioning system is warranted, such a positioning system can employ a video device to enable direct visualization of position of anchoring and device deployment. Such a system can also employ alternative approaches for verifying device position or presence over time, such as an RFID chip. Alternatively, a sizing balloon/catheter combination can be introduced before positioning of the actual device to get the distance between the area of device body deployment and the anchoring position. Alternatively, device body 210 or 228 can inflate temporarily or permanently to enable increased resistance at various anatomical landmarks, such as the LES, to confirm device position and presence. In yet a further embodiment, device 200 or an applicator thereof can contain a sensor that is used to locate the proper position of device body 210 or 228. For example a pH sensor can be used to identify the decrease in pH at the junction of the lower esophageal sphincter (LES) and the stomach, and used to position device body 210 or 228 in the LES region.

System 220 can also be used to deliver active agents or other therapeutic modalities to the sinuses, lungs and throat regions. Example diseases that can be treated with system 220 include allergic rhinitis, allergies, asthma, bronchitis, bronchospasm, candidiasis, chronic bronchitis, COPD, emphysema, hay fever, influenza, pharyngitis, pneumonia, respiratory tract infections, runny nose, sinus infections, sinusitis, sore throat, thrush, tonsillitis, and tuberculosis. Device body 210 or 228 can be floating in the stomach or pulled against the proximal surface of the stomach to recreate the effect of anti-obesity Lapband™ which also induces pressure on the proximal stomach wall.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLE

Reference is now made to the following example, which together with the above description, illustrate the invention in a non limiting fashion.

Figure 3:
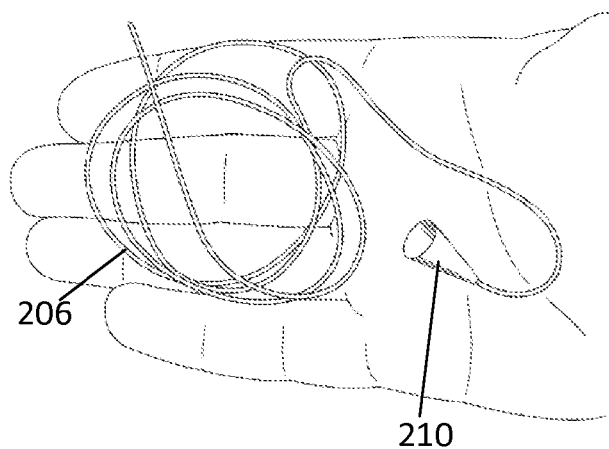
FIG. 3 is a photograph of an actual tethered anti-reflux device made of silicone.

With reference to FIG. 3, anti-reflux device body 210 in the form of a silicone cone 15 mm diameter and 0.5 mm thick walls was attached to elastic tether 206 made of silicone thread 1 mm diameter and 200 cm in length. Device body 210 was pushed into the left nostril of an adult subject using a 2 mm OD polyurethane delivery tube which had within its distal end a section of tether 206. When device body 210 was in the back of oropharynx, the subject drank a glass of water, which caused device body 210 to separate from the delivery tube and travel down the esophagus into the stomach of the subject. Tether 206 was cut outside the nostril and taped into position to the facial skin of the subject for the duration of this study.

Figure 4A:
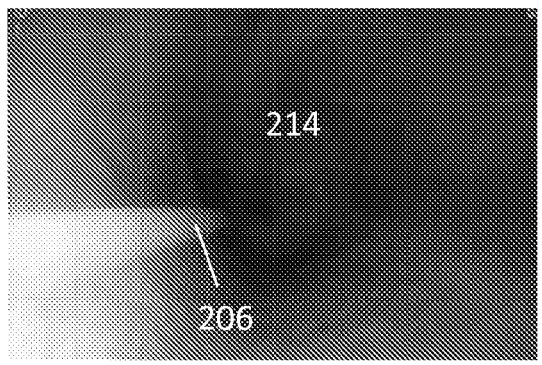
FIGS. 4A-D are endoscopic photographs of the tethered anti-reflux device in the stomach of a human subject.
Figure 4B:
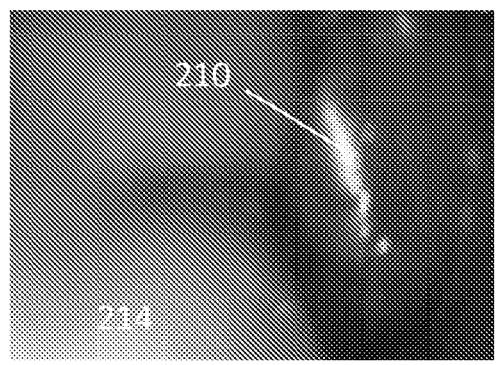
Figure 4C:
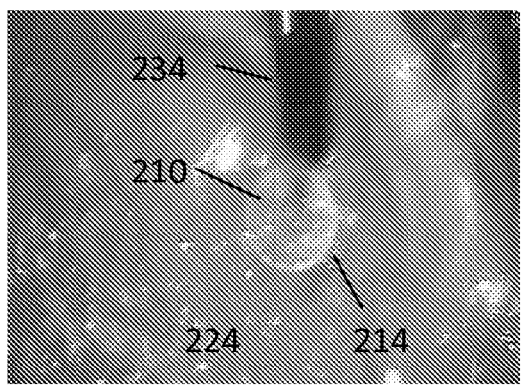
Figure 4D:
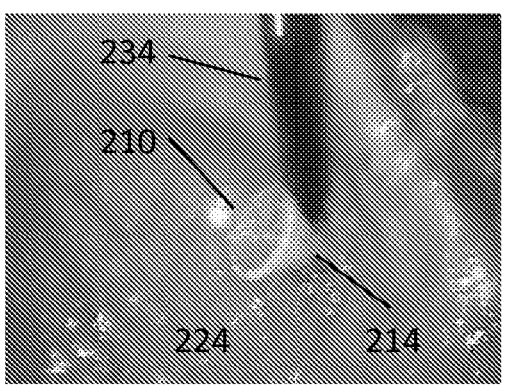

The delivery tube was removed and tether 206 was pulled back gently until resistance of device body 210 was felt against lower esophageal sphincter (LES) 214. A Pentax trans-nasal gastroscope was introduced via the left nostril of the subject in parallel to tether 206 and pushed into the stomach. FIG. 4a shows a view of tether 206 around 10 cm above LES 214. FIG. 4b shows device body 210 partially blocking the entrance of the esophageal lumen right at the level of LES 214. No resistance was felt introducing the gastroscope into the stomach since device body 210 moves away easily when pushed from above, such as when a bolus of food traverses LES 214 in the stomach. FIG. 4c shows from a retroflex perspective endoscope 234 emerging through LES 214 into stomach 224 of the subject, with device body 210 visible at the entrance to LES 214. It is clear from this figure how device body 210 acts as a conical shield or guard to prevent reflux from entering the subject's esophagus. FIG. 4d shows the same features, with device body 210 displaced slightly into stomach 224 showing its conical nature. Endoscope 234 was removed after taking the above-mentioned images. During this experiment, the subject did not feel any discomfort in having tether 206 or device body 210 implanted during the course of this study. The subject could also burp, but with increased resistance. The subject could also eat and drink normally. At the termination of the study, tether 206 was pulled out removing device body 210 from the subject altogether to end the fully reversible and non-invasive procedure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A therapeutic device comprising:
   (a) a conical device body being positionable within a stomach against a lower esophageal sphincter (LES); and
   (b) an elastic silicone tether having a Shore A value of 70 or less and being attachable at a first end to a tip of said conical device body and at a second end to a tissue region within the oral or nasal cavity to thereby position said device body against said LES, said tether and said device body being configured such that when said device body is positioned against said LES, it is capable of blocking reflux through said LES without interfering with passage of a food bolus through said LES.

2. The device of claim 1, wherein said tissue region within said nasal cavity is a nasal septum.

3. The device of claim 1, wherein said tether includes radiopaque markings.

4. The device of claim 1, wherein said device body is an open cone capable of assuming a collapsed or an expanded state.

5. The device of claim 4, wherein said collapsed state enables nasal delivery of said device body.

6. The device of claim 1, wherein a length of said elastic silicone tether corresponds to a distance between said tissue region within the oral or nasal cavity and said stomach.

* * * * *